(12) United States Patent
Wayland (10) Patent No.: US 8,288,445 B2
(45) Date of Patent: *Oct. 16, 2012

(54) STABLE PHARMACEUTICAL PRODUCTS

(75) Inventor: Ruth Wayland, Nantwich (GB)

(73) Assignee: Nycomed GmbH, Constance (DE)

( * ) Notice: Subject to any disclaimer, the term of this patent is extended or adjusted under 35 U.S.C. 154(b) by 0 days.

This patent is subject to a terminal disclaimer.

(21) Appl. No.: 12/951,608

(22) Filed: Nov. 22, 2010

(65) Prior Publication Data

US 2011/0064814 A1    Mar. 17, 2011

Related U.S. Application Data (63) Continuation of application No. 11/325,875, filed on Jan. 5, 2006, now Pat. No. 7,947,744, which is a continuation of application No. PCT/GB2004/002953, filed on Jul. 8, 2004.

(30) Foreign Application Priority Data

Jul. 8, 2003  (GB) .................................. 0315889.6

(51) Int. Cl.
| | | |
|---|---|---|
| A61K 31/05 | (2006.01) | |
| A61K 31/13 | (2006.01) | |
| A61K 31/136 | (2006.01) | |
| A61K 31/137 | (2006.01) | |
| A61K 31/16 | (2006.01) | |
| A61K 9/14 | (2006.01) | |
| A61K 9/12 | (2006.01) | |
| A61K 9/00 | (2006.01) | |
| A61M 13/00 | (2006.01) | |
| A61M 15/00 | (2006.01) | |

(52) U.S. Cl. ........ 514/731; 514/173; 514/174; 514/177; 514/178; 514/180; 514/613; 514/663; 514/734; 128/200.24

(58) Field of Classification Search .................. 514/173, 514/174, 177, 178, 180, 613, 663, 731, 734; 424/46, 489; 128/200.24
See application file for complete search history.

(56) References Cited

U.S. PATENT DOCUMENTS

| | | | |
|---|---|---|---|
| 4,342,603 A | 8/1982 | Daniels | |
| 4,816,445 A | 3/1989 | Mitsuhashi et al. | |
| 5,112,407 A | 5/1992 | Sakai et al. | |
| 5,192,528 A * | 3/1993 | Radhakrishnan et al. | 424/45 |
| 5,263,475 A | 11/1993 | Altermatt et al. | |
| 5,482,934 A | 1/1996 | Calatayud et al. | |
| 5,709,884 A | 1/1998 | Trofast et al. | |
| 6,040,344 A | 3/2000 | Gao et al. | |
| 6,268,533 B1 | 7/2001 | Gao et al. | |
| 6,472,563 B1 | 10/2002 | Tanoury et al. | |
| 6,475,467 B1 | 11/2002 | Keller et al. | |
| 6,645,466 B1 | 11/2003 | Keller et al. | |
| 6,866,839 B2 | 3/2005 | Aberg et al. | |
| 2002/0183293 A1 | 12/2002 | Banerjee et al. | |
| 2004/0231666 A1 | 11/2004 | Barker et al. | |

FOREIGN PATENT DOCUMENTS

| | | |
|---|---|---|
| DE | 195 41 689 A1 | 5/1996 |
| WO | 98/31351 A1 | 7/1998 |
| WO | 00/21487 A2 | 4/2000 |
| WO | 00/28979 A1 | 5/2000 |
| WO | 01/32163 A1 | 5/2001 |
| WO | 01/39745 A2 | 6/2001 |
| WO | 01/89491 A1 | 11/2001 |
| WO | 01/89492 A1 | 11/2001 |
| WO | 01/89616 A1 | 11/2001 |
| WO | 01/98174 A1 | 12/2001 |
| WO | 01/98175 A1 | 12/2001 |
| WO | 02/28368 A1 | 4/2002 |
| WO | 02/083113 A2 | 10/2002 |
| WO | 03/022275 A1 | 3/2003 |
| WO | 03/043905 A2 | 5/2003 |
| WO | 03/086349 A1 | 10/2003 |
| WO | 2004/052374 A1 | 6/2004 |
| WO | 2004/103379 A1 | 12/2004 |
| WO | 2004/105727 A2 | 12/2004 |
| WO | 2004/110460 A1 | 12/2004 |
| WO | 2005/034911 A1 | 4/2005 |
| WO | 2005/034927 A2 | 4/2005 |

OTHER PUBLICATIONS

Kirsch, et al., "Development of a Lyophilized Formulation for (R,R)-Formoterol (L)-Tartrate", Drug Development and Industrial Pharmacy, (2001), pp. 89-96, vol. 27, No. 1.
Dent, "Ciclesonide Byk Gulden", Current Opinion in Investigational Drugs, (2002), pp. 78-83, vol. 3, No. 1.
Belvisi, et al., "Soft Steroids: a new approach to the treatment of inflammatory airways diseases," Pulmonary Pharmacology & Therapeutics, (2003), pp. 321-325, vol. 16.
Armarego, et al., "Purification of Laboratory Chemicals," (1996), 4th Ed., Elsevier, pp. 28-29.
Braga, et al., "Making crystals from crystals: a green route to crystal engineering and polymorphism," Chem. Commun., (2005), pp. 3635-3645.
Vippagunta, et al., "Crystalline solids," Advanced Drug Delivery Reviews, (2001), pp. 3-26, vol. 48.

* cited by examiner

*Primary Examiner* — James H. Alstrum-Acevedo
(74) *Attorney, Agent, or Firm* — Nath, Goldberg & Meyer; Sheldon M. McGee

(57) ABSTRACT

Provided herein is a stable pharmaceutical product comprising a dry powder inhalation device, and a pharmaceutical composition that comprises R,R-Formoterol L-tartrate salt, in particular crystalline R,R-formoterol L-tartrate; and ciclesonide.

18 Claims, 1 Drawing Sheet

STABLE PHARMACEUTICAL PRODUCTS

This application is a continuation application of U.S. Ser. No. 11/325,875, filed Jan. 5, 2006, which is a continuation application of PCT/GB04/02953, filed Jul. 8, 2004.

FIELD OF THE INVENTION

The present invention relates to stable pharmaceutical products comprising a dry powder inhalation device, and a pharmaceutical composition within the device comprising R,R-formoterol L-tartrate salt, and in particular crystalline R,R-formoterol L-tartrate salt, as well as methods of making such products. More particularly, the present invention relates to pharmaceutical products having a pharmaceutical composition within a dry powder inhalation device comprising R,R-Formoterol L-tartrate salt, particularly crystalline R,R-formoterol L-tartrate salt, and ciclesonide, wherein the pharmaceutical composition is stable in the presence of a substance that could leach from a component of the device and induce R,R-formoterol L-tartrate salt, and in particular crystalline R,R-formoterol L-tartrate degradation.

BACKGROUND OF THE INVENTION

Formoterol, (+/−)N-[2-hydroxy-5-[1-hydroxy-2 [[2-(p-methoxyphenyl)-2-propyl]amino]ethyl]phenyl]-formamide, is a highly potent long lasting bronchodilator when inhaled. Formoterol has two chiral centers in the molecule, each of which can exist in two possible configurations. Thus, formoterol has four stereoisomers: (R,R), (S,S), (R,S) and (S,R). The racemic mixture that is commercially available for administration is a dihydrate of the fumarate salt. The order of potency of the isomers is (R,R)>>(R,S)=(S,R)>(S,S), and the (R,R)-isomer is 1000-fold more potent than the (S,S)-isomer. Administration of the pure (R,R)-isomer also offers an improved therapeutic ratio. U.S. Pat. No. 6,268,533 and PCT application WO 00/21487 disclose that the L-(+)-tartrate salt of R,R-formoterol is unexpectedly superior to other salts of R,R-formoterol, being easy to handle, pharmaceutically innocuous and non-hygroscopic. Also, U.S. Pat. No. 6,268,533 and U.S. Pat. No. 6,472,563, which are hereby incorporated by reference herein in their entireties, disclose that the L-tartrate salt of R,R-formoterol exists in three polymorphic forms, polymorph (A), (B), and (C).

Formoterol drug substances are known to be stable at ambient conditions for up to two years. However, when R,R-formoterol L-tartrate salt is mixed with lactose, degradation is known to occur (Maillards reaction) because of interactions between the amino groups within the R,R-formoterol L-tartrate salt molecule and the lactose moiety.

Dry powder inhalation devices usually need to be packed in a substantially impermeable package to prevent atmospheric moisture ingress. The use of such impermeable packages may cause accumulation of certain trace substances within the sealed local environment to a level sufficient for them to interact with the pharmaceutical composition contained in the dry powder inhalation device. Such interaction, for example, may result in an adduct between the pharmaceutical composition and the trace substance, resulting in the formation of degradation products. For instance, a dry powder inhaler generally includes a number of plastic components molded from an acetal homopolymer, and the plastic components may contain trace formaldehyde formed as a breakdown product during the molding of acetal resins. It is believed that the trace formaldehyde released from the plastic components is capable of forming an adduct with various pharmaceutical compositions when packaged within a substantially impermeable container.

Accordingly, what is needed is a stable pharmaceutical product comprising R,R-formoterol L-tartrate salt, and in particular crystalline R,R-formoterol L-tartrate salt, in a dry powder inhalation device, wherein the degradation of R,R-formoterol L-tartrate salt is reduced or eliminated.

The citation of any reference herein should not be construed as an admission that such reference is available as "Prior Art" to the instant application.

SUMMARY OF THE INVENTION

Provided herein is a novel and useful stable pharmaceutical product in which the degradation of R,R formoterol L-tartrate salt, and in particular crystalline R,R-formoterol L-tartrate salt, due to interaction with a substance that leaches from a component of a dry powder inhalation device of the stable pharmaceutical product, or as a result of a Maillard reaction between R,R formoterol L-tartrate salt, particularly crystalline R,R-formoterol L-tartrate salt, and a pharmaceutically acceptable carrier, e.g. a reducing sugar, is reduced or eliminated.

Broadly, the present invention extends to a stable pharmaceutical product that comprises a dry powder inhalation device, an effective amount of a sorbent material, a pharmaceutical composition within the device that comprises (i) crystalline R,R-formoterol L-tartrate salt, and (ii) ciclesonide. A stable pharmaceutical product of the present invention also comprises a sealed package that forms a chamber within which the dry powder inhalation device, sorbent material, and pharmaceutical composition are situated.

Moreover, the present invention extends to a stable pharmaceutical product comprising a dry powder inhalation device, a porous sachet containing an effective amount of 10 Å molecular sieves, and a pharmaceutical composition within the device, which comprises crystalline R,R-formoterol L-tartrate salt; ciclesonide; and a reducing sugar. The device and the porous sachet are contained in a volume enclosed by a sealed package.

The present invention also extends to a stable pharmaceutical product comprising:
a) a dry powder inhalation device;
b) a porous sachet enclosing 4 grams of 10 Å molecular sieves;
c) a pharmaceutical composition within the device comprising:
  (i) crystalline R,R-formoterol L-tartrate salt, wherein the crystalline R,R-formoterol L-tartrate salt has a particle size of about 0.1 µm to about 10 µm;
  (ii) ciclesonide; and
  (iii) non-micronized lactose monohydrate; and
d) a sealed package having an enclosed volume within which the device, the sachet and the pharmaceutical composition are situated.

Furthermore, in a pharmaceutical composition of a stable pharmaceutical product of the present invention, the particle size of the crystalline R,R-formoterol L-tartrate salt can vary. For example, the particle size can be about 0.1 µm to about 10 µm. In a particular embodiment, about 95% of the particles of the crystalline R,R-formoterol L-tartrate salt have a particle size less than about 5 µm.

The present invention also extends to a stable pharmaceutical product as described herein, wherein the pharmaceutical composition further comprises a pharmaceutically acceptable carrier. Numerous pharmaceutically acceptable carriers have applications herein. A particular example is a reducing sugar, such as lactose, glucose, mannose, galactose, maltose, xylose, cellobiose, mellibiose, maltotriose, etc., as well as hydrates thereof. In a particular embodiment, the reducing sugar is lactose or lactose monohydrate. Moreover, a reducing sugar having applications herein as a pharmaceutically acceptable carrier need not be micronised. Naturally, the particle size of a pharmaceutically acceptable carrier of a stable product of the present invention can vary. In an embodiment of the present invention comprising a pharmaceutically effective carrier, which is a reducing sugar, the size of the particles can range from about 0.5 µm to about 350 µm, from about 0.5 µm to about 315 µm, from about 0.5 µm to about 150 µm, from about 0.5 µm to about 100 µm, from about 0.5 µm to about 45 µm, from about 0.5 µm to about 25 µm, from about 0.5 µm to about 10 µm, from about 5 µm to about 350 µm, from about 5 µm to about 315 µm, from about 5 µm to about 150 µm, from about 5 µm to about 100 µm, from about 5 µm to about 45 µm, from about 5 µm to about 25 µm, from about 5 µm to about 100 µm, from about 10 µm to about 350 µm, from about 10 µm to about 315 µm, from about 10 µm to about 150 µm, from about 10 µm to about 100 µm, from about 10 µm to about 45 µm, from about 10 µm to about 25 µm, from about 25 µm to about 350 µm, from about 25 µm to about 315 µm, from about 25 µm to about 150 µm, from about 25 µm to about 100 µm, from about 25 µm to about 45 µm, from about 45 µm to about 350 µm, from about 45 µm to about 315 µm, from about 45 µm to about 150 µm, from about 45 µm to about 100 µm, from about 100 µm to about 350 µm from about 100 µm to about 315 µm, from about 100 µm to about 150 µm, from about 150 µm to about 350 µm, from about 150 µm to about 315 µm, from about 315 µm to about 350 µm. In a particular embodiment, the pharmaceutically acceptable carrier is a non-micronised reducing sugar, e.g. lactose monohydrate, having particles of a mean particle size of about 41 µm.

The present invention further extends to a stable pharmaceutical product as described herein, wherein the ratio of pharmaceutically acceptable carrier to R,R-formoterol L-tartrate salt, and in particular crystalline R,R-formoterol L-tartrate salt, can vary in a pharmaceutical composition of the stable pharmaceutical product. In an embodiment of the present invention, the ratio is about 2969 µg to about 3016 µg of pharmaceutically acceptable carrier per about 0.5 µg to about 4 µg of R,R-formoterol L-tartrate salt, e.g. crystalline R,R-formoterol L-tartrate salt. In a more particular embodiment, a pharmaceutical composition comprises about 2969 µg to about 3016 µg of pharmaceutically acceptable carrier per about 1 µg to about 2 µg of R,R-formoterol L-tartrate salt, and in particular crystalline R,R-formoterol L-tartrate salt; and in a still more particular embodiment, a pharmaceutical composition comprises about 2969 µg to about 3016 µg of pharmaceutically acceptable carrier per about 1 µg of R,R-formoterol L-tartrate salt, more particularly crystalline R,R-formoterol L-tartrate salt.

Also, the present invention extends to a stable pharmaceutical product as described herein, wherein the sealed package is substantially impermeable to moisture. Numerous materials for producing such a sealed package have applications in a stable pharmaceutical product of the present invention, e.g. metal, glass, a flexible laminate, plastic, or a combination thereof, to name only a few. In particular, a sealed package of a stable pharmaceutical product of the present invention can be made from a flexible laminate comprising three layers: an inner layer, a barrier layer, and an outer layer. Numerous materials can be used for the outer layer, including paper or a polymer, such as polyester. Likewise, the barrier layer, which is moisture impermeable, can be made of a variety of materials, such as a polymer or a metal, e.g. aluminum, copper, steel, zinc, iron, tin, magnesium an amalgam, etc., to name only a few. The inner layer can also be made of a variety of materials that can undergo heat sealing. In a particular embodiment of a stable pharmaceutical product of the present invention, the flexible laminate comprises a 12 micron polyester outer layer, a 9 micron aluminum barrier layer, and a 50 micron polyethylene inner layer. An adhesive holds each layer in place. The sealing of a package of a stable pharmaceutical product can be accomplished in a variety of ways. More specifically, heat-sealing, gluing, welding, brazing, mechanical closures, mechanical clamps, or compression can hermetically seal a sealed package of a stable pharmaceutical product of the present invention.

Moreover, a sealed package of a stable pharmaceutical product of the present invention can be a bottle, a bag, a drum box or an irregularly shaped container. In a particular embodiment, the sealed package is made of plastic.

Furthermore, the present invention extends to a stable pharmaceutical product as described herein, having various configurations. For example, in a stable pharmaceutical product of the present invention, the dry powder inhalation device can comprise a multi-dose reservoir that contains the pharmaceutical composition. Naturally though, the present invention also encompasses unit dose systems and capsule-containing systems.

In addition, a component of a dry powder inhalation device of a stable pharmaceutical product of the present invention can be comprised of a variety of materials, including a polymer, e.g. polyacetal, polypropylene, polyacrylamide, polycarbonate, polyethylene, polyurethane, a copolymer, etc. Moreover, a component of a dry powder device of a stable pharmaceutical product of the present invention may leach a substance capable of causing degradation of R,R-formoterol L-tartrate salt, and in particular crystalline R,R-formoterol L-tartrate salt. In a particular embodiment, at least one component of the dry powder inhalation device of a stable pharmaceutical product of the present invention comprises polyacetal, which leaches formaldehyde.

A stable pharmaceutical product of the present invention also comprises an effective amount of a sorbent material. Examples of sorbent material having applications herein include, but certainly are not limited to molecular sieves, activated clays, charcoal, activated alumina, silica, zeolites, bauxites or any mixture thereof. Moreover, the sorbent material can be located in various places in a stable pharmaceutical product of the present invention. For example, an effective amount of sorbent material can be housed within the dry powder inhalation device. Alternatively, the effective amount of sorbent material can be incorporated into a polymer mixture and manufactured into a component of the powder inhalation device. In still another example, the effective amount of sorbent material can be held in a porous sachet. The effective amount of sorbent material can also be incorporated into an adhesive, or into plastic sheeting used in the packaging of a stable pharmaceutical product of the present invention. In a particular embodiment of a stable pharmaceutical product of the present invention, the sorbent material is a 10 Å molecular sieve.

Accordingly, it is an aspect of the present invention to provide a novel stable pharmaceutical product having a pharmaceutical composition comprising R,R-formoterol L-tartrate salt, and in particular crystalline R,R-formoterol L-tartrate salt, and ciclesonide, wherein degradation of R,R-formoterol L-tartrate salt, and particularly crystalline R,R-formoterol L-tartrate salt, and the formation of impurities, e.g. an adduct, arising from the interaction of the R,R-formoterol L-tartrate salt, in particular crystalline R,R-formoterol L-tartrate salt. with a material that leaches from a component of the device, e.g. formaldehyde, is reduced or eliminated.

This and other aspects of the present invention will be better appreciated by reference to the following drawing and Detailed Description.

BRIEF DESCRIPTION OF THE FIGURE

FIG. 1 also details the comparable stability of the DPI comprising of ciclesonide, lactose monohydrate and crystalline R,R-formoterol L-tartrate salt when stored for 2 months at 25 degrees Celsius and 60% humidity and also at 4 degrees Celsius and ambient humidity.

DETAILED DESCRIPTION

The present invention is based on the discovery that, surprisingly and unexpectedly, the addition of a sorbent material that adsorbs or absorbs (or a combination of both) with respect to a substance that leaches from a component of a dry powder inhalation device of a stable pharmaceutical product of the present invention reduces or eliminates the formation of adducts due to the interaction of R,R-formoterol L-tartrate salt, and in particular crystalline R,R-formoterol L-tartrate salt, contained within a pharmaceutical composition and the substance. Thus the present invention extends various embodiments described below:

1] A stable pharmaceutical product comprising:
  a) a dry powder inhalation device;
  b) an effective amount of a sorbent material;
  c) a pharmaceutical composition within the device comprising:
    (i) R,R-formoterol L-tartrate salt; and
    (ii) ciclesonide; and
  d) a sealed package having an enclosed volume within which the device, the sorbent material and the pharmaceutical composition are situated.

[2] The stable pharmaceutical product of Embodiment [1], wherein the R,R-formoterol L-tartrate salt is crystalline R,R-formoterol L-tartrate salt.

[3] The stable pharmaceutical product of either of Embodiments [1] or [2], wherein the dry powder inhalation device comprises a multi-dose reservoir that contains the pharmaceutical composition.

[4] The stable pharmaceutical product of any of Embodiments [1]-[3] wherein a component of the dry powder inhalation device leaches a substance capable of causing degradation of the R,R-formoterol L-tartrate salt.

[5] The stable pharmaceutical product according to Embodiment [4], wherein the component of the device comprises polyacetal material, and the substance is formaldehyde.

[6] The stable pharmaceutical product of any of Embodiments [1]-[5], wherein the dry powder inhalation device is an "ULTRAHALER" device.

[7] The stable pharmaceutical product of any of Embodiments [1]-[6], wherein the sorbent material is housed within the dry powder inhalation device.

[8] The stable pharmaceutical product of any of Embodiments [1]-[7], wherein the sorbent material is incorporated into a polymer mixture and manufactured into a component of the dry powder inhalation device.

[9] The stable pharmaceutical product of any of Embodiments [1]-[6], wherein the sorbent material is incorporated into plastic sheeting used in packaging the dry powder inhalation device.

[10] The stable pharmaceutical product of any of Embodiments [1]-[7], wherein the sorbent material is incorporated into an adhesive.

[11] The stable pharmaceutical product of any of Embodiments [1]-[6], wherein the sorbent material is in a porous sachet.

[12] The stable pharmaceutical product of any of Embodiments [1]-[11], wherein the sorbent material is selected from the group consisting of: a molecular sieve, activated clay, charcoal, activated alumina, silica, a zeolite, a bauxite, and a mixture thereof.

[13] The stable pharmaceutical product of any of Embodiments [1]-[12], wherein the sorbent material is 10 Å molecular sieves.

[14] The stable pharmaceutical product of any of Embodiments [1]-[13], wherein the R,R-formoterol L-tartrate salt has a particle size of about 0.1 µm to about 10 µm.

[15] The stable pharmaceutical product of any of Embodiments [1]-[14], wherein greater than about 95% of the R,R-formoterol L-tartrate salt has a particle size of less than about 5 µm.

[16] The stable pharmaceutical product of any of Embodiments [1]-[15], wherein the pharmaceutical composition further comprises a pharmaceutically acceptable carrier.

[17] The stable pharmaceutical product of Embodiment [16], wherein the pharmaceutical composition comprises about 2969 µg to about 3016 µg of the pharmaceutically acceptable carrier per about 0.5 µg to about 4 µg of R,R-formoterol L-tartrate salt.

[18] The stable pharmaceutical product of either of Embodiments [16] or [17], wherein the pharmaceutical composition comprises about 2969 µg to about 3016 µg of the pharmaceutically acceptable carrier per about 1 µg to about 2 µg of R,R-formoterol L-tartrate salt.

[19] The stable pharmaceutical product of any of Embodiments [16]-[18], wherein the pharmaceutical composition comprises about 2969 µg to about 3016 µg of the pharmaceutically acceptable carrier per about 1 µg of R,R-formoterol L-tartrate salt.

[20] A stable pharmaceutical product comprising:
  a) a dry powder inhalation device;
  b) an effective amount of a sorbent material;
  c) a pharmaceutical composition within the device comprising:
    (i) crystalline R,R-formoterol L-tartrate salt; and
    (ii) ciclesonide; and
  d) a sealed package having an enclosed volume within which the device, the sorbent material and the pharmaceutical composition are situated.

[21] The stable pharmaceutical product of Embodiment [20], wherein the dry powder inhalation device comprises a multi-dose reservoir that contains the pharmaceutical composition.

[22] The stable pharmaceutical product of either of Embodiments [20] or [21], wherein a component of the dry powder inhalation device leaches a substance capable of causing degradation of the crystalline R,R-formoterol L-tartrate salt.

[23] The stable pharmaceutical product according to Embodiment [22], wherein the component of the device comprises polyacetal material, and the substance is formaldehyde.

[24] The stable pharmaceutical product of any of Embodiments [20]-[23], wherein the dry powder inhalation device is an "ULTRAHALER" device.

[25] The stable pharmaceutical product of any of Embodiments [20]-[24], wherein the sorbent material is housed within the dry powder inhalation device.

[26] The stable pharmaceutical product of any of Embodiments [20]-[25], wherein the sorbent material is incorporated into a polymer mixture and manufactured into a component of the dry powder inhalation device.

[27] The stable pharmaceutical product of any of Embodiments [20]-[24], wherein the sorbent material is incorporated into plastic sheeting used in packaging the dry powder inhalation device.

[28] The stable pharmaceutical product of any of Embodiments [20]-[25], wherein the sorbent material is incorporated into an adhesive.

[29] The stable pharmaceutical product of any of Embodiments [20]-[24], wherein the sorbent material is in a porous sachet.

[30] The stable pharmaceutical product of any of Embodiments [20]-[29], wherein the sorbent material is selected from the group consisting of: a molecular sieve, activated clay, charcoal, activated alumina, silica, a zeolite, a bauxite, and a mixture thereof.

[31] The stable pharmaceutical product of any of Embodiments [20]-[30], wherein the sorbent material is 10 Å molecular sieves.

[32] The stable pharmaceutical product of any of Embodiments [20]-[31], wherein the crystalline R,R-formoterol L-tartrate salt has a particle size of about 0.1 μm to about 10 μm.

[33] The stable pharmaceutical product of any of Embodiments [20]-[32], wherein greater than about 95% of the crystalline R,R-formoterol L-tartrate salt has a particle size of less than about 5 μm.

[34] The stable pharmaceutical product of any of Embodiments [20]-[33], wherein the pharmaceutical composition further comprises a pharmaceutically acceptable carrier.

[35] A stable pharmaceutical product comprising:
  a) a dry powder inhalation device;
  b) an effective amount of a sorbent material;
  c) a pharmaceutical composition within the device comprising:
    (i) crystalline R,R-formoterol L-tartrate salt;
    (ii) ciclesonide, and
    (iii) a pharmaceutically acceptable carrier; and
  d) a sealed package having an enclosed volume within which the device, the sorbent material and the pharmaceutical composition are situated.

[36] The stable pharmaceutical product of Embodiment [35], wherein the dry powder inhalation device comprises a multi-dose reservoir that contains the pharmaceutical composition.

[37] The stable pharmaceutical product of either of Embodiments [35] or [36], wherein a component of the dry powder inhalation device leaches a substance capable of causing degradation of the crystalline R,R-formoterol L-tartrate salt.

[38] The stable pharmaceutical product according to embodiment [37], wherein the component of the device comprises polyacetal material, and the substance is formaldehyde.

[39] The stable pharmaceutical product of any of Embodiments [35]-[38], wherein the dry powder inhalation device is an "ULTRAHALER" device.

[40] The stable pharmaceutical product of any of Embodiments [35]-[39], wherein the sorbent material is housed within the dry powder inhalation device.

[41] The stable pharmaceutical product of any of Embodiments [35]-[40], wherein the sorbent material is incorporated into a polymer mixture and manufactured into a component of the dry powder inhalation device.

[42] The stable pharmaceutical product of any of Embodiments [35]-[40], wherein the sorbent material is incorporated into plastic sheeting used in packaging the dry powder inhalation device.

[43] The stable pharmaceutical product of any of Embodiments [35]-[40], wherein the sorbent material is incorporated into an adhesive.

[44] The stable pharmaceutical product of any of Embodiments [35]-[39], wherein the sorbent material is in a porous sachet.

[45] The stable pharmaceutical product of any of Embodiments [35]-[44], wherein the sorbent material is selected from the group consisting of: a molecular sieve, activated clay, charcoal, activated alumina, silica, a zeolite, a bauxite, and a mixture thereof.

[46] The stable pharmaceutical product of any of Embodiments [35]-[45], wherein the sorbent material is 10 Å molecular sieves.

[47] The stable pharmaceutical product of any of Embodiments [35]-[46], wherein the crystalline R,R-formoterol L-tartrate salt has a particle size of about 0.1 mm to about 10 μm.

[48] The stable pharmaceutical product of any of Embodiments [35]-[47], wherein greater than about 95% of the crystalline R,R-formoterol L-tartrate salt has a particle size of less than about 5 μm.

[49] The stable pharmaceutical product of any of Embodiments [16]-[19], [34]-[48], wherein the pharmaceutically acceptable carrier is a reducing sugar.

[50] The stable pharmaceutical product of Embodiment [49], wherein the reducing sugar is not micronised.

[51] The stable pharmaceutical product of either of Embodiments [49] or [50], wherein the reducing sugar has a mean particle size of about 41 mm.

[52] The stable pharmaceutical product of any of Embodiments [49]-[51], wherein the reducing sugar is selected from the group consisting of lactose, glucose, mannose, galactose, maltose, xylose, cellobiose, mellibiose, maltotriose, a hydrate of lactose, a hydrate of glucose, a hydrate of mannose, a hydrate of galactose, a hydrate of maltose, a hydrate of xylose, a hydrate of cellobiose, a hydrate of mellibiose, a hydrate of maltotriose, and a combination thereof.

[53] The pharmaceutical product of any of Embodiments [49]-[52], wherein the reducing sugar is lactose.

[54] The stable pharmaceutical product of any of Embodiments [49]-[53], wherein the reducing sugar is lactose monohydrate.

[55] The stable pharmaceutical product of any of Embodiments [34]-[54], wherein the pharmaceutical composition comprises about 2969 μg to about 3016 μg of the pharmaceutically acceptable carrier per about 0.5 μg to about 4 μg of crystalline R,R-formoterol L-tartrate salt.

[56] The stable pharmaceutical product of any of Embodiments [34]-[55], wherein the pharmaceutical composition comprises about 2969 μm to about 3016 μg of the pharmaceutically acceptable carrier per about 1 μg to about 2 μg of crystalline R,R-formoterol L-tartrate salt.

[57] The stable pharmaceutical product of any of Embodiments [34]-[56], wherein the pharmaceutical composition comprises about 2969 μg to about 3016 μg of the pharmaceutically acceptable carrier per about 1 μg of crystalline R,R-formoterol L-tartrate salt.

[58] The stable pharmaceutical product of any of Embodiments [34]-[57], wherein the pharmaceutically acceptable carrier is non-micronized lactose monohydrate having a particle size of about 41 μm.

[59] A stable pharmaceutical product comprising:
   a) a dry powder inhalation device;
   b) a porous sachet enclosing an effective amount of 10 Å molecular sieves;
   c) a pharmaceutical composition within the device comprising:
      (i) crystalline R,R-formoterol L-tartrate salt;
      (ii) ciclesonide; and
      (iii) a reducing sugar; and
   d) a sealed package having an enclosed volume within which the device, the sachet and the pharmaceutical composition are situated.

[60] The stable pharmaceutical product of Embodiment [59], wherein the reducing sugar is not micronised.

[61] The stable pharmaceutical product of either of Embodiments [59] or [60], wherein the reducing sugar has a mean particle size of about 41 μm.

[62] The stable pharmaceutical product of any of Embodiments [59]-[61], wherein the reducing sugar is selected from the group consisting of lactose, glucose, mannose, galactose, maltose, xylose, cellobiose, mellibiose, maltotriose, a hydrate of lactose, a hydrate of glucose, a hydrate of mannose, a hydrate of galactose, a hydrate of maltose, a hydrate of xylose, a hydrate of cellobiose, a hydrate of mellibiose, a hydrate of maltotriose, and a combination thereof.

[63] The pharmaceutical product of any of Embodiments [59]-[62], wherein the reducing sugar is lactose.

[64] The stable pharmaceutical product of any of Embodiments [59]-[63], wherein the reducing sugar is lactose monohydrate.

[65] The stable pharmaceutical product of any of Embodiments [59]-[64], wherein the pharmaceutical composition comprises about 2969 μg to about 3016 μg of the reducing sugar per about 0.5 μg to about 4 μg of crystalline R,R-formoterol L-tartrate salt.

[66] The stable pharmaceutical product of any of Embodiments [59]-[65], wherein the pharmaceutical composition comprises about 2969 μg to about 3016 μg of the reducing sugar per about 1 μg to about 2 μg of crystalline R,R-formoterol L-tartrate salt.

[67] The stable pharmaceutical product of any of Embodiments [59]-[66], wherein the pharmaceutical composition comprises about 2969 μg to about 3016 μg of the reducing sugar per about 1 μg of crystalline R,R-formoterol L-tartrate salt.

[68] The stable pharmaceutical product of any of Embodiments [65]-[67], wherein the reducing sugar is non-micronized lactose monohydrate having a particle size of about 41 μm.

[69] The stable pharmaceutical product of any of Embodiments [59]-[68], wherein the crystalline R,R-formoterol L-tartrate salt has a particle size of about 0.1 μm to about 10 μm.

[70] The stable pharmaceutical product of any of Embodiments [59]-[68], wherein greater than about 95% of the crystalline R,R-formoterol L-tartrate salt has a particle size of less than about 5 μm.

[71] The stable pharmaceutical product of any of Embodiments [59]-[70], wherein the effective amount of molecular sieves is 4 g.

[72] A stable pharmaceutical product comprising:
   a) a dry powder inhalation device;
   b) a porous sachet enclosing 4 grams of 10 Å molecular sieves;
   c) a pharmaceutical composition within the device comprising:
      (i) crystalline R,R-formoterol L-tartrate salt, wherein the crystalline R,R-formoterol L-tartrate salt has a particle size of about 0.1 μm to about 10 μm;
      (ii) ciclesonide; and
      (iii) non-micronized lactose monohydrate; and
   d) a sealed package having an enclosed volume within which the device, the sachet and the pharmaceutical composition are situated.

[73] The stable pharmaceutical product of Embodiment [72], wherein the pharmaceutical composition comprises about 2969 μg to about 3016 μg of the non-micronized lactose monohydrate per about 0.5 μg to about 4 μg of crystalline R,R-formoterol L-tartrate salt.

[74] The stable pharmaceutical product of either of Embodiments [72]-[73], wherein the pharmaceutical composition comprises about 2969 μg to about 3016 μg of the non-micronized lactose monohydrate per about 1 μg to about 2 μg of crystalline R,R-formoterol L-tartrate salt.

[75] The stable pharmaceutical product of any of Embodiments [72]-[74], wherein the pharmaceutical composition comprises about 2969 μg to about 3016 μg of the non-micronized lactose monohydrate per about 1 μg of crystalline R,R-formoterol L-tartrate salt.

[76] The stable pharmaceutical product of any of Embodiments [72]-[75], wherein greater than about 95% of the crystalline R,R-formoterol L-tartrate salt has a particle size of less than about 5 μm.

[77] The stable pharmaceutical product of any of Embodiments [1]-[76], wherein the sealed package is substantially impermeable to moisture.

[78] The stable pharmaceutical product of any of Embodiments [1]-[77], wherein the sealed package is made of metal, glass, or plastic, and has a configuration selected from the group consisting of a bottle, a bag, a drum box, and an irregularly shaped container.

[79] The stable pharmaceutical product of any of Embodiments [1]-[78], wherein the sealed package is made of plastic.

[80] The stable pharmaceutical product of any of Embodiments [1]-[79], wherein the sealed package is a flexible laminate comprising an inner layer, a barrier layer, and an outer layer, wherein the barrier layer is located between the inner layer and the outer layer.

[81] The stable pharmaceutical product of Embodiment [80], wherein the inner layer is polyethylene, the barrier layer is a metal foil, wherein the metal is selected from the group consisting of aluminum, copper, steel, zinc, tin, magnesium, and an amalgam thereof, and the outer layer comprises polyester or paper.

[82] The stable pharmaceutical product of Embodiment [81], wherein the flexible laminate comprises a 12 micron polyester outer layer, a 9 micron aluminum foil barrier layer, and a 50 micron polyethylene inner layer.

[83] The stable pharmaceutical product of any of Embodiments [1]-[82], wherein the sealed package is hermetically sealed using heat-sealing, glue, a weld, brazing the sealed package, a mechanical closure or clamp, or compression of the sealed package.

It is appreciated that certain features of the invention, which are, for clarity, described in the context of separate embodiments, may also be provided in combination in a single embodiment. Also, various features of the invention that are, for brevity, described in the context of a single embodiment, may also be provided separately or in any suitable subcombination.

Moreover, numerous terms and phrases are used throughout the instant Specification and Claims in accordance with the present invention. Therefore, if appearing herein, the following terms and phrases shall have the definitions set out below.

As used herein, the term "stable" refers to a pharmaceutical composition in a stable pharmaceutical product of the present invention that does not substantially decompose to form degradation products, e.g. adducts, when stored in a sealed package at about 40° C. at about 75% relative humidity for at least 2 months.

As used herein, the term "dry powder inhalation device" refers to a breath activated device for administering a dry powder into the lungs of a subject. More particularly, a dry powder inhalation device may have a component that gradually leaches a substance that can degrade crystalline R,R-formoterol L-tartrate salt, wherein the device is contained within a sealed package. The sealed package may be substantially impermeable so that a substance released from a component of the dry powdered inhalation device of a stable pharmaceutical product of the present invention, e.g. formaldehyde that leaches from a polyacetal component, may accumulate in the package and/or the device. Therefore, the present invention is not limited to any specific type of dry powder inhalation device as long as there is a potential for a component of the device to leach a substance, e.g. formaldehyde gas, that interacts with R,R,-formoterol L-tartrate salt, and in particular crystalline R,R-formoterol L-tartrate salt to form adducts. Examples are described infra.

As used herein, the term "component" refers to a component of a dry powder inhalation device, wherein the component releases a material that can induce R,R-formoterol L-tartrate salt degradation, and more particularly crystalline R,R-formoterol L-tartrate salt degradation. In a particular embodiment of the present invention, at least one component of a dry powder inhalation device comprises a polyacetal material (polyoxymethylene). Polyoxymethylene (polyacetal plastics—Trade Names: DELRIN (DuPont), ULTRAFORM (the Ultraform Co.), and HOSTAFORM (Ticona)) are a group of plastics produced by polymerizing formaldehyde. Polyoxymethylene is used in toiletry and cosmetic articles as well as medical devices such as inhalers and syringes. A number of dry powder inhalation device components are manufactured from polyacetal plastic that is known to contain residual formaldehyde formed during the molding process e.g. the "ULTRAHALER" device-Aventis Pharma Ltd, UK, and those devices described in U.S. Pat. No. 5,176,132 and U.S. Pat. No. 5,678,538; and U.S. Provisional Patent Application No. 60/417,534. Polyacetal is readily available from a number of commercial sources, for example Sigma-Aldrich, Milwaukee, Wis. 53201.

As used herein, the term "sealed package" refers to a container that is substantially impermeable to moisture and to a substance released from a component of a dry powder inhalation device, such as formaldehyde released from a polyacetal component. Such a package may be made of metal, glass, or plastic, and can have a conformation selected from the group consisting of bottles, bags, drum boxes, and irregularly shaped containers. For example, a sealed package of the present invention can be a conventional flexible package, and its manufacturing is well known to those of ordinary skill in the art. Generally, such a flexible package can be constructed from flat reels of laminate, which are folded or otherwise formed according to the packaging equipment technology, into a package by means of sealing and cutting. In a particular embodiment of the present invention, the sealed package is a substantially impermeable flexible package in which are sealed a dry powder inhalation device and a sorbent material, e.g. a molecular sieve, enclosed in a porous sachet. In such an embodiment, the sealed package is constructed from a flat reel of flexible material, which is curled around into a long tube. The edges of the tube are heated (welded) together forming a seal. The cross seals are formed by a straight heater bar, which clamps the laminate tube in front of and behind the package contents (i.e., the dry powder inhalation device and sorbent sachet). It also cuts the continuous tube into individual packs. As a result, there is a long continuous seal down the middle of the pack and the cross seals at both ends. Also, in another embodiment the package has a substantially impermeable flexible package, in which a dry powder inhalation device and sorbent material are situated. The sorbent material can be molded as part of one of the plastic components of the dry powder inhalation device of a pharmaceutical product of the present invention, or can be provided in a container that is fixed to a dry powder inhalation device.

A flexible package used in making a sealed package of the present invention generally comprises several layers of materials either co-extruded or bonded together to form an apparently single film of "laminate". Such a film of laminate may have three layers adhesively laminated to each other: an inner layer, a barrier layer and an outer layer. The inner layer forms the inside of the package (in contact with the dry powder inhalation device) and is normally a thermoplastic layer and heat-sealable. A common material for the inner layer is polyethylene, but other polyolefinic or cyclo-olefinic materials may also be used. In addition, special materials such as ionomers are also used for making the inner layer. A particular example of such an ionomer is "SURLYN".

The barrier layer is situated between the inner and outer layers and provides impermeability to the pack. Aluminum foil is commonly used for the barrier layer, although any metal capable of being rolled into thin sheets can also be satisfactorily used. Other examples of applicable metals include, but certainly are not limited to copper, steel, zinc, iron, tin, magnesium an amalgam, etc., to name only a few. A typical thickness for the foil barrier layer is about 8 or 9 microns. Alternatively, the barrier layer may be a metalized film comprising tin, iron, zinc, magnesium or other metals coated by vacuum deposition or sputtering onto a polymeric sheet.

The outer layer normally provides support, impact resistance, and protection for the barrier, layer, and generally conveys robustness to the pack. A commonly used material for the outer layer is polyester, although another material, such as paper, may also be used.

Most flexible laminate materials for packaging are commercially available. For example, Pharmaflex Ltd., part of Alcan Inc. (Cramlington, Northumberland, England) supplies a laminate film having three layers: 12 micron polyester 19 micron aluminum foil/50 micron polyethylene (product catalog LMP-F BRI/72/H1), wherein the aluminum foil layer is between the polyester and polyethylene layers.

In addition to a flexible sealed package, other types of sealed packages have applications in the present invention, provided they are substantially impermeable to moisture ingress. In general, when a sealed package or enclosure is impermeable or substantially impermeable to moisture, it is also impermeable or substantially impermeable to a substance that leaches from a component of a dry powder inhalation device of a pharmaceutical product of the present invention, e.g. formaldehyde gas, when a component comprises polyacetal. As explained above, formaldehyde has the potential to interact with R,R-formoterol L-tartrate salt, and in particular crystalline R,R-formoterol L-tartrate salt, in a dry powder inhalation device of a stable pharmaceutical product of the present invention, resulting in degradation of the R,R-formoterol L-tartrate salt, and in particular crystalline R,R-formoterol L-tartrate salt, and formation of adducts.

As used herein, the term "R,R-formoterol L-tartrate salt degradation" refers to any process that causes a decrease in the amount of R,R-formoterol L-tartrate salt present a pharmaceutical composition of a stable pharmaceutical product of the present invention, and in particular causes a decrease in the amount of crystalline R,R-formoterol L-tartrate salt present in a pharmaceutical composition of a stable pharmaceutical product of the present invention. Such a process includes, but certainly is not limited to, the reaction of formaldehyde gas that leaches from a component of a dry powder inhalation device that comprises polyacetal, with R,R-formoterol L-tartrate salt, and in particular crystalline R,R-formoterol L-tartrate salt, to form an adduct. Another process that contributes to degradation of R,R-formoterol L-tartrate salt, particularly crystalline R,R-formoterol L-tartrate salt, is a Maillard reaction with a pharmaceutically acceptable carrier, particularly a reducing carrier, e.g. lactose.

As used herein, the term "adduct" refers to a compound formed by the reaction of R,R-formoterol L-tartrate salt, and in particular crystalline R,R-formoterol L-tartrate salt, of a pharmaceutical composition of a stable pharmaceutical product of the present invention with a substance that has leached from a component of a dry powder inhalation device of a stable pharmaceutical product of the present invention. In a particular embodiment in which the component comprises polyacetal, the substance that leaches is formaldehyde. Although under no obligation to disclose a mechanism that results in the production of an adduct, and certainly not intending to be bound to any hypothesis, it is believed at least two possible mechanisms are responsible for adduct formation with formaldehyde. The first is direct contact between the R,R-formoterol L-tartrate salt, e.g. crystalline R,R-formoterol L-tartrate salt, and formaldehyde that has leached from a component of the dry powder inhalation device that comprises polyacetal, which inherently contains residual formaldehyde. The second is a reaction between the R,R, formoterol L-tartrate salt, such as crystalline R,R-formoterol L-tartrate salt, and gaseous formaldehyde within the inner local environment of the sealed package, wherein the gaseous formaldehyde has been released from the polyacetal components and has accumulated in the local environment to a significant level due to the substantial impermeability of the sealed package. The term "adduct" may also refer to a compound formed by the reaction of R,R-formoterol L-tartrate salt, and in particular crystalline R,R-formoterol L-tartrate salt, with a reducing sugar, i.e. a product of the Maillard Reaction.

The term "sorbent material" refers to a material that has the ability to condense or hold molecules of other substances on its surface, or within its inner structure. Such activities are often referred as "absorbance" and "absorbance", respectively. Thus, a sorbent material of the present invention can adsorb, absorb, or perform a combination of both. Examples of sorbent material having applications herein include activated carbon, alumina, bauxite, charcoal, a zeolite, silica gel, a molecular sieve, activated clay, or any mixture thereof, etc. In a particular embodiment of the present invention, wherein a component of the dry powder inhalation device comprises polyacetal, the sorbent material adsorbs or absorbs (or a combination thereof) formaldehyde that leaches from the component so that the formaldehyde is unable to react with R,R-formoterol L-tartrate salt, and in particular crystalline R,R-formoterol L-tartrate salt, to form adducts.

The present invention is not limited to any specific sorbent material. Choosing a proper sorbent material, as well its effective amount for a particular embodiment of the present invention is well within the skill of one of ordinary skill in the art, and may require, at most, the performance of certain routine laboratory techniques. Applicants have found that the most effective sorbent material for an embodiment of the present invention, where at least one component of a dry powder inhalation device comprises polyacetal, is a molecular sieve with a pore size of about 10 Angstroms. Inclusion of 1 to 10 grams of the molecular sieve, for example, supplied by AtoFina (Solihull, England) under the trade name SILIPORITE, is a particular molecular sieve having applications as a sorbent material. Molecular sieves can also be purchased from Linde, Air Products, etc. More detailed technical information about molecular sieves and their industrial uses can be found in the Molecular Sieves: Unique Moisture and Odor-Taste Control Material", D. Hajdu, T. J. Dangieri and S. R. Dunne, *TAPPI Polym., Laminations Coat. Conf.* (1999), Vol. 2, p. 655-662, which is hereby incorporated by reference herein in its entirety.

There are numerous ways in which a sorbent material can be incorporated into a pharmaceutical product of the present invention. For example, the sorbent material can be incorporated into a polymer mixture and manufactured into a plastic component of a dry powder inhalation device of a pharmaceutical product of the present invention, or manufactured into plastic sheeting used in the packaging of the device. Furthermore, the sorbent material can be incorporated into a polymer mixture in the same, or similar manner as desiccant polymer mixtures disclosed in U.S. Pat. Nos. 5,911,937; 3,245,946, 4,013,566, 4,407,897; 4,425,410; 4,464,443; 5,078,909; and 4,792,484, which are hereby incorporated by reference herein in their entireties. Moreover, a sorbent material can be incorporated into a stable pharmaceutical product of the present invention in an adhesive (e.g. a self-adhesive patch or tape), in the same, or similar, manner as adhesive desiccants disclosed in U.S. Pat. No. 6,103,141, which is hereby incorporated by reference herein in its entirety. The sorbent material can also be within a cavity in a dry powder inhalation device (i.e. housed in the device) of a stable pharmaceutical product of the present invention, or situated inside a cap or body of a dry-powder inhaler. Furthermore, the sorbent material can be incorporated into a component of a dry powder inhalation device, such as a cap, body, or a portion thereof in the form of a polymer mixture. The sorbent material can be affixed to a dry powder inhalation device of a stable pharmaceutical product of the present invention in the form of an adhesive sticker/tape that comprises the sorbent material. In another example, the sorbent material can be separate from a dry powder inhalation device in an enclosed volume within which the device is situated.

A sorbent material of a stable pharmaceutical product of the invention can also be in a porous sachet. Such a sachet need not be in a sealed package. However though, in a particular embodiment of the present invention, a porous sachet having the sorbent material is contained within a sealed package. Sorbent sachets are commercially available from a variety of suppliers, such as Sud-Chemie (Middlewich, England). The sachet, with a "tea-bag" like appearance, is generally manufactured from synthetic fibers, such as polyamide or polyester fibers or blends thereof. Commercially available materials suitable for making sorbent sachets include, for example, "GDT-H" from San-ei Corporation (Osaka, Japan), and "TYVEK" from Perfecseal (Londonderry N. Ireland U.K.). However, a suitable sachet may be in other convenient shapes or appearances, and be made from other permeable materials.

As used herein, the phrase "effective amount of a sorbent material" refers to the amount of an sorbent material sufficient to adsorb or absorb (or a combination thereof) a substance that leaches from a component of a dry powder inhalation device of a stable pharmaceutical product of the present invention, in order to reduce or eliminate the formation of adducts with R,R, formoterol L-tartrate salt, and in particular crystalline R,R-formoterol L-tartrate salt, of a pharmaceutical composition of a stable pharmaceutical product of the present invention. In a particular embodiment, wherein a component of the dry powder inhalation device comprises polyacetal, the substance that leaches from the component is formaldehyde. The effective amount of sorbent material will depend on a number of factors, including the type of sorbent material used, and the number of components of the dry powder inhalation device that leach the substance. One of ordinary skill in the art can readily determine the effective amount of sorbent material for a stable pharmaceutical product of the present invention using routine laboratory techniques.

Pharmaceutical Composition

As explained above, a pharmaceutical composition of a stable pharmaceutical product of the present invention comprises R,R-formoterol L-tartrate salt, particularly R,R-formoterol L-tartrate salt; and ciclesonide.

A pharmaceutical composition of a stable pharmaceutical product of the present invention can also comprise a pharmaceutically acceptable carrier. As used herein, the phrase "pharmaceutically acceptable" refers to molecular entities and compositions that are physiologically tolerable and do not typically produce an allergic or similar untoward reaction, such as gastric upset, dizziness and the like. Particularly, as used herein, the phrase "pharmaceutically acceptable" means approved by a regulatory agency of the Federal or a state government, or listed in the U.S. Pharmacopeia, or other generally recognized pharmacopeia for use in animals, and more particularly in humans. The term "carrier" refers to a diluent, adjuvant, excipient, or vehicle with which an active compound(s) is (are) administered. Examples of pharmaceutical carriers are described in "Remington's Pharmaceutical Sciences" by E. W. Martin.

A stable pharmaceutical product of the present invention comprises, inter alia, a pharmaceutical composition for pulmonary administration, and may include diluents of various buffer content (e.g., Tris-HCl, acetate, phosphate), pH and ionic strength; additives such as detergents and solubilizing agents (e.g., Tween 80, Polysorbate 80), anti-oxidants (e.g., ascorbic acid, sodium metabisulfite), preservatives (e.g., Thimersol, benzyl alcohol) and bulking substances (e.g., lactose, mannitol); incorporation of the material into particulate preparations of polymeric compounds such as polylactic acid, polyglycolic acid, etc., or into liposomes. Hylauronic acid may also be used. Such compositions may influence the physical state, stability, rate of in vivo release. See, e.g., Remington's Pharmaceutical Sciences, 18th Ed. (1990, Mack Publishing Co., Easton, Pa. 18042) pages 1435-1712, which are herein incorporated by reference. The compositions may be prepared in liquid form, or may be in dried powder, such as lyophilized form.

Contemplated for use in the present invention are a wide variety of dry powder inhalation devices designed for pulmonary delivery of a pharmaceutical composition comprising R,R-formoterol L-tartrate salt, particularly crystalline R,R-formoterol L-tartrate salt, and ciclesonide, all of which are familiar to those skilled in the art.

Some specific examples of commercially available devices suitable for the practice of the present invention are the SPINHALER powder inhaler, manufactured by Fisons Corp., Bedford, Mass., the AEROLIZER inhaler produced by Novartis, and the ULTRAHALER device produced by Aventis Pharma, Ltd. to name only a few. Other examples of dry powder inhalation devices having applications in a stable pharmaceutical product of the present invention include those described in U.S. Pat. No. 5,176,132 and U.S. Pat. No. 5,678,538, and U.S. Provisional Patent Application No. 60/417,534, which are hereby incorporated by reference herein in their entireties. In a particular embodiment, the dry powder inhalation device is the ULTRAHALER.

All dry powder inhalations presently available or subsequently developed require the use of formulations suitable for the dispensing of a pharmaceutical composition comprising R,R-formoterol L-tartrate salt, particularly crystalline R,R-formoterol L-tartrate salt, and ciclesonide. Typically, each formulation is specific to the type of device employed, and may involve the use of an appropriate adjuvant and/or carrier useful in therapy.

A particular example of a pharmaceutically acceptable carrier having applications herein is a reducing sugar such as lactose, glucose, mannose, galactose, maltose, xylose, cellobiose, mellibiose, maltotriose, etc., as well as hydrates thereof, in amounts which facilitate dispersal of the powder from the device. As used herein, the term "reducing sugar" refers to a carbohydrate that undergoes oxidation and is able to reduce a metal ion to a lower oxidation state. In particular, a reducing sugar having applications as a pharmaceutically acceptable carrier is lactose. More particularly, the reducing sugar is lactose monohydrate. A particular grade of lactose having applications here is RESPITOSE ML001 (DMV, Veghel, The Netherlands). Moreover, a reducing sugar having applications herein as a pharmaceutically acceptable carrier need not be micronised.

Naturally, the particle size of a pharmaceutically acceptable carrier of a pharmaceutical composition of a stable pharmaceutical product of the present invention can vary. In an embodiment of the present invention which further comprises a reducing sugar as a pharmaceutically effective carrier, the size of the particles can range from about 0.5 μm to about 350 μm, from about 0.5 μm to about 315 μm, from about 0.5 μm to about 150 μm, from about 0.5 μm to about 100 μm, from about 0.5 μm to about 45 μm, from about 0.5 μm to about 25 μm, from about 0.5 μm to about 10 μm, from about 5 μm to about 350 μm, from about 5 μm to about 315 μm, from about 5 μm to about 150 μm, from about 5 μm to about 100 μm, from about 5 μm to about 45 μm, from about 5 μm to about 25 μm, from about 5 μm to about 10 μm, from about 10 μm to about 350 μm, from about 10 μm to about 315 μm, from about 10 μm to about 150 μm, from about 10 μm to about 100 μm, from about 10 μm to about 45 μm, from about 10 μm to about 25 μm, from about 25 μm to about 350 μm, from about 25 μm to about 315 μm, from about 25 μm to about 150 μm, from about 25 μm to about 100 μm, from about 25 μm to about 45 μm, from about 45 μm to about 350 μm, from about 45 μm to about 315 μm, from about 45 μm to about 150 μm, from about 45 μm to about 100 μm, from about 100 μm to about 350 μm from about 100 μm to about 315 μm, from about 100 μm to about 150 μm, from about 150 μm to about 350 μm, from about 150 μm to about 315 μm, from about 315 μm to about 350 μm. In a particular embodiment, the pharmaceutically acceptable carrier is non-micronised lactose monohydrate having particles of a mean particle size of about 41 µm.

The particle size of R,R-formoterol L-tartrate salt, and particular crystalline R,R-formoterol L-tartrate salt of a pharmaceutical composition, as well ciclesonide, can vary. For example, the particle size of the R,R-formoterol L-tartrate, and in particular crystalline R,R-formoterol L-tartrate salt, can be about 0.1 µm to about 10 µm. In a particular embodiment, about 95% of the particles have a particle size less than about 5 µm, for most effective delivery to the distal lung.

Furthermore, the ratio of pharmaceutically acceptable carrier to R,R-formoterol L-tartrate salt, particularly crystalline R,R-formoterol L-tartrate salt, can vary in a pharmaceutical composition of a stable pharmaceutical product of the present invention. In an embodiment of the present invention, the ratio is about 2969 µg to about 3016 µg of pharmaceutically acceptable carrier per about 0.5 µg to about 4 µg of R,R-formoterol L-tartrate salt, particularly crystalline R,R-formoterol L-tartrate. In a more particular embodiment, a pharmaceutical composition comprises about 2969 µg to about 3016 µg of pharmaceutically acceptable carrier per about 1 µg to about 2 µg of R,R-formoterol L-tartrate salt, particularly crystalline R,R-formoterol L-tartrate salt; and in a still more particular embodiment, a pharmaceutical composition comprises about 2969 µg to about 3016 µg of pharmaceutically acceptable carrier per about 1 µg of R,R-formoterol L-tartrate salt, particularly crystalline R,R-formoterol L-tartrate salt.

Generally, the amount of ciclesonide in a pharmaceutical composition of a stable pharmaceutical product of the present invention should be in sufficient quantity so that at a daily dose range of from 20 to 1600 µg can be administered to a patient. Exemplary doses in connection with invention comprise 20, 40, 60, 80, 100, 120, 140, 160, 180, 200, 320 µg of ciclesonide, and in particular, the dose comprises 40, 80, 160 or 320 µg ciclesonide. The dose is preferably a daily dose and a pharmaceutical composition of a stable pharmaceutical product of the present invention can be administered once or twice daily, particularly once daily. A once daily dose may be administered any time of the day, e.g. in the morning or preferably in the evening. The administration of a daily close of in the range of from 20 to 320 µg of ciclesonide is preferably part of a continuous treatment regimen, preferably a treatment period of more than one day, particularly preferably more than one week, e.g. a two week treatment period, a one month treatment period, a one year treatment period or a life long treatment period.

While there have been described and pointed out fundamental novel features of the present invention as applied to particular embodiments thereof, it will be understood that various omissions and substitutions and changes, in the form and details of the packages, sorbent materials and their location, pharmaceutical compositions, and methods, may be made by those of ordinary skill in the art without departing from the spirit of the invention. For example, it is expressly intended that all combinations of those elements and/or method steps, which perform substantially the same function in substantially the same way to achieve the same results, are within the scope of the present invention.

The present invention may be better understood by reference to the following non-limiting Example, which is provided as exemplary of the invention. The following Example is presented in order to more fully illustrate a particular embodiment of the present invention. It should in no way be construed, however, as limiting the broad scope of the present invention.

EXAMPLE

A feasibility study to assess performance and stability of a pharmaceutical composition comprising crystalline R,R-formoterol tartrate salt and ciclesonide in a dry powder inhaler in comparison with a pharmaceutical composition comprising R,S-formoterol fumarate dihydrate and ciclesonide has been performed. The particular inhaler used in this study was the ULTRAHALER produced by Aventis Pharma Ltd. UK Preparation of Pharmaceutical Ultrahalers Two ULTRAHALERS were prepared. One contained a pharmaceutical composition comprising crystalline R,R-formoterol L-tartrate salt, ciclesonide, and non-micronized lactose monohydrate as a pharmaceutically acceptable carrier. The other contained a pharmaceutical composition comprising R,S-formoterol fumarate dihydrate, ciclesonide, and non-micronized lactose monohydrate as a pharmaceutical carrier. A method for producing such ULTRAHALERS is set forth below:

1. Deaggregate both lactose monohydrate and drug substances (separately).
2. Add the lactose monohydrate, ciclesonide and formoterol (either crystalline R,R-formoterol L-tartrate salt or R,S-formoterol fumarate dihydrate, depending upon which pharmaceutical product is being produced) into the mixing drum.
3. Mix the composition for approximately 7 minutes
4. Fill the blend into a dry powder inhalation device (ULTRAHALER—Aventis Pharma Ltd, UK) using a filling machine (e.g. fill weight limits 2.5-2.7 g)
5. after being filled, wrap the dry powder inhalation device with molecular sieves inside a laminate foil overwrap (i.e. 12 micron polyester/9 micron aluminum foil/50 micron polyethylene), using conventional means.

Stability Testing

A blend of Ciclesonide (19.97 mg/g), crystalline R,R formoterol L-tartrate salt (0.3 mg/g) and non-micronized lactose monohydrate (979.70 mg/g) were blended in a tumble mixer for several minutes. Another blend of Ciclesonide (19.97 mg/g), R,S-formoterol fumarate dihydrate (0.3 mg/g) and non-micronized lactose monohydrate (979.70 mg/g) was also blended for several minutes. Each blend was then separately filled into an Aventis ULTRAHALER device using a filling machine. The filled ULTRAHALER devices were then wrapped in an laminate foil overwrap with a molecular sieve porous sachet (4 g of 10 Å molecular sieves). Three wrapped ULTRAHALERs containing the pharmaceutical composition comprising crystalline R,R-formoterol L-tartrate salt were produced. One was stored at 40° Celsius and 75% relative humidity, another was stored at 25 degrees Celsius and 60% relative humidity and the third was stored at 4 degrees Celsius and ambient humidity, each of which were stored for 2 months. An ULTRAHALER device containing a pharmaceutical composition comprising R,S-formoterol fumarate dihydrate was stored at 40 degrees Celsius and 75% relative humidity, for 2 months The amount of degradation in the samples stored at these conditions were measured by HPLC using the following analytical conditions:

| Column: | Hipersil BDS-C18, 5 µm particle size, 150 mm × 4.6 mm i.d. |
|---|---|
| Column temperature: | Ambient |
| Mobile phase A composition: | 30% Ammonium Acetate (pH 8.0 ± 0.05), 55% Water, 15% Acetonitrile |
| Mobile phase B composition: | 300 Ammonium Acetate (pH 8.0 ± 0.05): 750 Acetonitrile |

Gradient Time Table

| Time (min) | % A | % B |
|---|---|---|

-continued

|   |     |     |
|---|-----|-----|
| 0 | 100 | 0   |
| 10 | 100 | 0  |
| 20 | 87  | 13  |
| 30 | 70  | 30  |
| 40 | 70  | 30  |
| 40.1 | 0 | 100 |
| 53.0 | 0 | 100 |
| 53.1 | 100 | 0 |

Flow rate: 1.0 ml/minute
Detection: 250 nm

Figure 1:
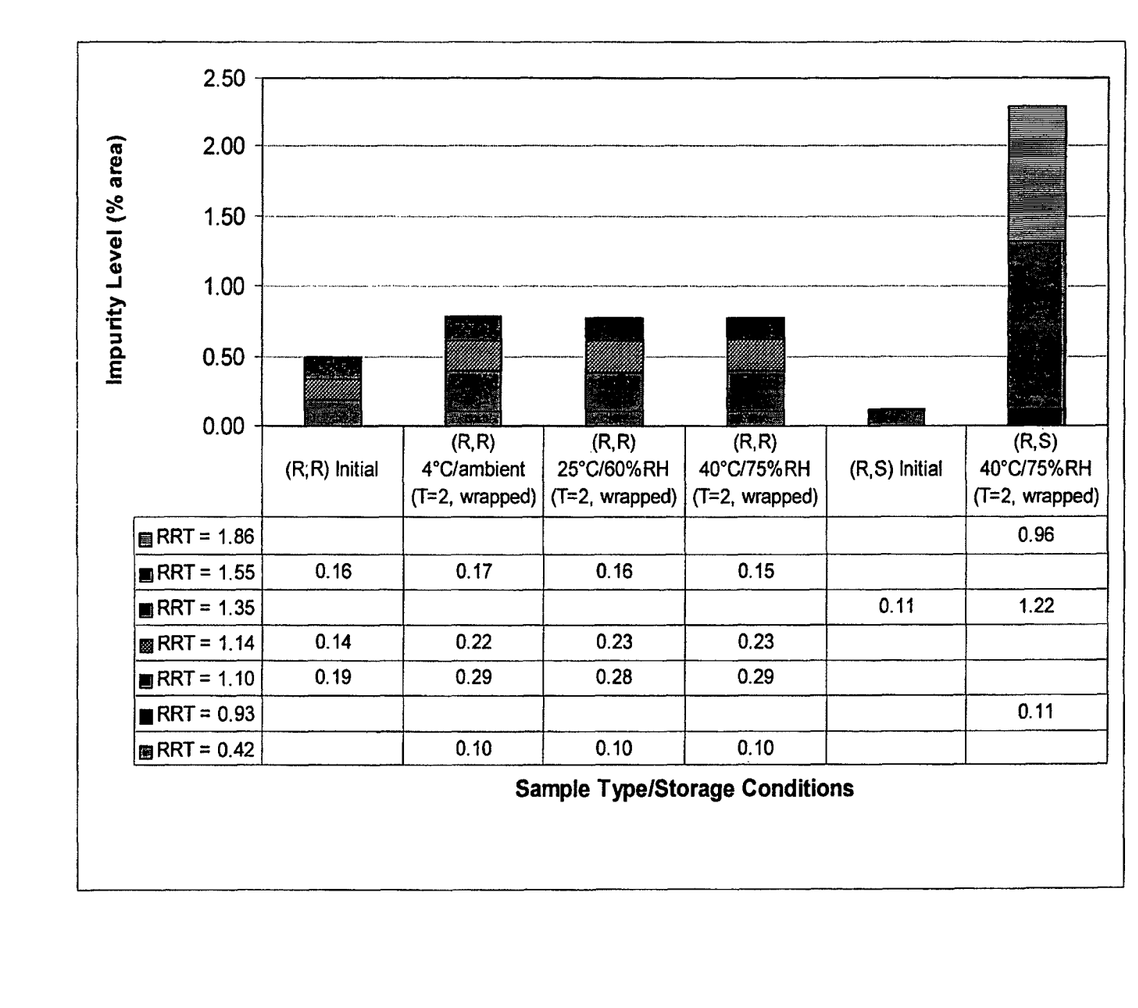
FIG. 1: Histogram summary of stability data that shows the enhanced stability of a dry powder inhaler (DPI) comprising of ciclesonide, non-micronised lactose monohydrate and crystalline R,R formoterol L-tartrate salt stored for 2 months at 40 degrees Celsius and 75% humidity compared to a DPI comprising of ciclesonide, lactose monohydrate and R,S-formoterol fumarate dihydrate stored at the same conditions, where in the DPI are wrapped in the presence of a molecular sieve.

Results:

The results of this stability test, graphically shown in FIG. 1, show that at the initial crystalline R,R stability time point, three degradents were identified at Relative Retention Times (RRT)=1.10, RRT=1.14 and RRT=1.55 at levels of 0.19, 0.14 and 0.16% area, respectively. During storage of the DPI's at 40 degrees Celsius and 75% relative humidity, 25 degrees Celsius and 60% relative humidity, and 4 degrees Celsius and ambient humidity for 2 months, the levels of the degradents increased consistently across the storage conditions with an additional degradent being detected at RRT=0.42. This is in stark contrast to the levels of degradation observed with the same product manufactured using R,S formoterol fumarate dihydrate stored at 40 degrees Celsius and 75% relative humidity, wherein impurities are detected at different RRT's (RRT=0.93, RRT=1.35 and RRT=1.86). The total degradation of the R,S formoterol fumarate product is 2.29% area compared to 0.67% area in the crystalline R,R formoterol tartrate product at the 2 months stability time point when stored at 40 degrees Celsius and 75% relative humidity, where the initially 0.49% area total degradation was detected. This data clearly demonstrates the increased stability of the crystalline R,R-formoterol L-tartrate salt pharmaceutical product compared to the R,S formoterol fumarate product.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Various publications are cited herein, the disclosures of which are incorporated by reference in their entireties.

What is claimed is:

1. A stable pharmaceutical product comprising:
   a) a pharmaceutical composition comprising:
      (i) R,R-formoterol L-tartrate salt; and
      (ii) ciclesonide;
   b) an article which comprises a material that leaches a substance that is capable of causing degradation of the R,R-formoterol L-tartrate salt;
   c) an effective amount of a sorbent material; and
   d) a sealed package having an enclosed volume within which said pharmaceutical composition, said article and said sorbent material are situated.

2. The stable pharmaceutical product of claim 1, wherein said R,R-formoterol L-tartrate salt is crystalline R,R-formoterol L-tartrate salt.

3. The stable pharmaceutical product of claim 1, wherein said material is polyoxymethylene.

4. The stable pharmaceutical product of claim 1, wherein said substance is formaldehyde.

5. The stable pharmaceutical product according to claim 1, wherein said article is a dry powder inhalation device.

6. The stable pharmaceutical product of claim 5, wherein said dry powder inhalation device comprises a multi-dose reservoir that contains said pharmaceutical composition.

7. The stable pharmaceutical product of claim 5, wherein said sorbent material is housed within said dry powder inhalation device.

8. The stable pharmaceutical product of claim 5, wherein said sorbent material is incorporated into a polymer mixture and manufactured into a component of said dry powder inhalation device.

9. The stable pharmaceutical product of claim 5, wherein said sorbent material is incorporated into plastic sheeting used in packaging said dry powder inhalation device.

10. The stable pharmaceutical product of claim 1, wherein said sorbent material is incorporated into an adhesive.

11. The stable pharmaceutical product of claim 1, wherein said sorbent material is in a porous sachet.

12. The stable pharmaceutical product of claim 1, wherein said sorbent material is selected from the group consisting of: a molecular sieve, activated clay, charcoal, activated alumina, silica, a zeolite, a bauxite, and a mixture thereof.

13. The stable pharmaceutical product of claim 1, wherein said sorbent material is 10 Å molecular sieves.

14. The stable pharmaceutical product of claim 1, wherein said R,R-formoterol L-tartrate salt has a particle size of about 0.1 μm to about 10 μm.

15. The stable pharmaceutical product of claim 1, wherein greater than 95% or about 95% of said R,R-formoterol L-tartrate salt has a particle size of less than 5 μm or about 5 μm.

16. The stable pharmaceutical product of claim 1, wherein said pharmaceutical composition further comprises a pharmaceutically acceptable carrier.

17. The stable pharmaceutical product of claim 16, wherein said pharmaceutical composition comprises about 2969 μg to about 3016 μg of said pharmaceutically acceptable carrier per about 0.5 μg to about 4 μg of R,R-formoterol L-tartrate salt.

18. The stable pharmaceutical product of claim 16, wherein said pharmaceutical composition comprises about 2969 μg to about 3016 μg of said pharmaceutically acceptable carrier per about 1 μg to about 2 μg of R,R-formoterol L-tartrate salt.

* * * * *